United States Patent [19]

Stein et al.

[11] Patent Number: 5,520,906
[45] Date of Patent: May 28, 1996

[54] TRIAZINE DERIVATIVES WITH UV FILTER PROPERTIES

[75] Inventors: Ingeborg Stein, Erzhausen; Michael Casutt, Heppenheim; Ulrich Heywang, Darmstadt; Roland Martin, Weinheim; Michael Schwarz, Gross-Gerau, all of Germany

[73] Assignee: Merck Patent Gesellschaft Mit Beschrankter Haftung, Darmstadt, Germany

[21] Appl. No.: 284,596

[22] PCT Filed: Feb. 1, 1993

[86] PCT No.: PCT/EP93/00226

§ 371 Date: Aug. 12, 1994

§ 102(e) Date: Aug. 12, 1994

[87] PCT Pub. No.: WO93/17002

PCT Pub. Date: Sep. 2, 1993

[30] Foreign Application Priority Data

Feb. 19, 1992 [DE] Germany .................. 42 04 923.7
Jul. 21, 1992 [DE] Germany .................. 42 23 890.0

[51] Int. Cl.⁶ .................. A61K 7/42; A61K 7/44; C07D 251/30; C07D 251/54
[52] U.S. Cl. .................. 424/59; 424/60; 514/241; 514/245; 544/194; 544/197; 544/208; 544/211; 544/219
[58] Field of Search ............ 424/59, 60; 514/241, 514/245; 544/194, 197, 208, 211, 219

[56] References Cited

U.S. PATENT DOCUMENTS

| | | | |
|---|---|---|---|
| 4,061,730 | 12/1977 | Kalopissis et al. | 424/59 |
| 5,037,568 | 8/1991 | O'Neil et al. | 544/219 |
| 5,252,323 | 10/1993 | Richard et al. | 544/197 |

FOREIGN PATENT DOCUMENTS

| | | |
|---|---|---|
| 0087098 | 8/1983 | European Pat. Off. . |
| 0457687 | 11/1991 | European Pat. Off. . |
| 0507692 | 10/1992 | European Pat. Off. . |
| 4223890 | 8/1993 | Germany .................. 544/197 |

*Primary Examiner*—Yogendra N. Gupta
*Attorney, Agent, or Firm*—Millen, White, Zelano and Branigan

[57] ABSTRACT

Triazine compounds of the formula I

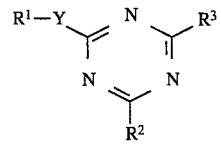

wherein
Y is NH or O,
$R^1$ in each case independently of one another are a radical of the formula II

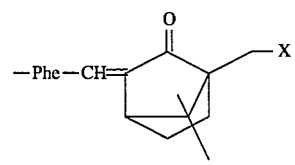

wherein
Phe is a phenylene group which is unsubstituted or substituted by 1 to 4 alkyl or alkoxy groups having 1 to 10 C atoms and
X is H or $-SO_3H$,
and
$R^2$ and $R^3$
  in each case independently of one another are a radical of the formula $Y-R^1$,
or
alkoxy, alkylamino, arylamino or aryloxy having 1 to 10 C atoms. Also, cosmetic formulations, medicaments and pharmaceutical formulations containing the compounds, particularly as filters for solar rays.

20 Claims, No Drawings

TRIAZINE DERIVATIVES WITH UV FILTER PROPERTIES

The invention relates to triazine derivatives of the Formula I

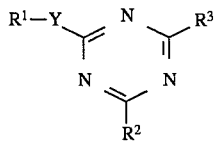

wherein
Y is NH or O,
R¹ in each case independently of one another are a radical of the formula II

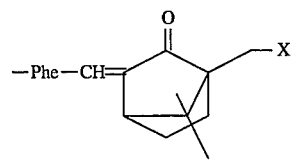

wherein
Phe is a phenylene group which is unsubstituted or substituted by 1 to 4 alkyl or alkoxy groups having 1 to 10 C atoms and
X is H or —SO₃H,
and
R² and
R³ are a radical of the formula Y-R¹,
or
  alkoxy, alkylamino, arylamino or aryloxy having 1 to 10 C atoms,
and processes for their preparation and their use in cosmetic formulations, in particular for protection from solar radiation, and in pharmaceutical formulations for preventive treatment of inflammations and allergies of the skin or of certain types of cancer.

As is known, the skin reacts sensitively to solar rays, which can cause common sunburn or erythema, but also burns to a greater or lesser degree.

However, solar rays also have other adverse effects: they cause the skin to lose its elasticity and form wrinkles and thus lead to premature ageing. Dermatoses can also sometimes be observed. In extreme cases, skin cancer occurs in some people.

It is also desirable to protect hair from photochemical damage, to prevent changes in color shades, decolorization or damage of a mechanical nature.

It is known that the components contained in cosmetic preparations are not always sufficiently stable to light and decompose under the action of light rays.

It is known that the most dangerous part of solar rays is formed by the ultraviolet rays having a wavelength of less than 400 nm. It is also known that, because of the presence of the ozone layer in the earth's atmosphere, which absorbs some of the solar radiation, the lower limit of the ultraviolet rays which reach the earth's surface is about 280 nm.

It therefore seems desirable to provide compounds which can absorb UV rays in a wavelength range from 280 to 400 nm, that is to say also UV-B rays having a wavelength between 280 and 320 nm, which play a decisive role in the development of solar erythema, and also UV-A rays having a wavelength of between 320 and 400 nm, which tan the skin but also age it, promote initiation of an erythematous reaction or magnify this reaction in certain people or can even trigger phototoxic or photoallergic reactions.

The sunscreen filters customary today in cosmetics are divided into UVA filters and UVB filters. While there are good filters in the UVB range (280–320 nm) with substances such as Eusolex® 6300 or Eusolex® 232, those used in the UVA range (320–400 nm) have problems:

Dibenzoylmethanes such as Parsol® 1789 or Eusolex® 8020 do not have an unlimited stability under UV irradiation, which on the one hand reduces the effectiveness of the filter with time and on the other hand can promote photosensitizations of the skin in isolated cases. The benzophenones also used as UVA filters have only a limited solubility in the oils used in cosmetics, and they have a relatively low absorption. In contrast, only few water-soluble UVA filters are currently known, but their UV absorption is low.

Similar triazine derivatives are known from DE 34 08 406. However, these contain no methylenecamphylidene group on the phenylene ring. Although these compounds can also be used as UV filters in sunscreen agents, they show no absorption in the UVA range. These compounds furthermore have only a limited solubility in conventional cosmetic carriers, in particular in aqueous suspensions, so that they usually have to be employed together with other UV filters in sunscreen agents.

German Auslegeschrift DE 12 05 970 describes triazine derivatives for protection of organic substances from UV radiation, the triazine group in these derivatives being linked to a benzooxazolylanilino group. These compounds absorb UV rays with high wavelengths, for example 370–380 nm, and are unsuitable as constituents of cosmetic compositions.

It has been found that (4-camphylidenemethylene-anilino or -phenoxy)-1,3,5-triazine derivatives, in particular 1,3,5-triazines which are linked to aminoarylidenecamphor in the 2,4- or in the 2,4,6-position, have outstanding UVA filter properties. Their solubility in the oils used in cosmetics is very good, so that use concentrations up to at least 10% of the formulation are possible even in complicated formulations. Sulfonic acid derivatives (X=SO₃H) are a water-soluble form of the new filter. The water-solubility here is so good that use concentrations of 10% are likewise possible.

The compounds according to the invention furthermore have an exceptional photostability with respect to UV radiation, which by far exceeds the stability of the UV filter substances known to date.

If the extinction in the UVB range has a minimum, this is not a disadvantage, since a UVB filter can also be incorporated into the formulation without problems.

The compounds of the formula I furthermore can also be used for the preventive treatment of inflammations and allergies of the skin and for prevention of certain types of cancer.

In addition to their good properties as filters, the compounds according to the invention are distinguished by a good heat and photochemical stability.

These compounds furthermore offer the advantage of not being toxic or irritating and of being completely harmless to the skin.

They disperse uniformly in the conventional cosmetic carriers and, in fat carriers in particular, can form a continuous film; they can be applied to the skin in this manner in order to form an effective protective film.

The invention relates to the compounds of the abovementioned formula I, in particular wherein Phe is 1,4-phenylene.

Preferred embodiments of the present invention are:

a) Triazine derivatives of the formula I1

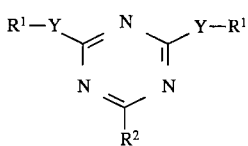

wherein $R^1$, $R^2$ and Y have the meaning given;
b) Triazine derivatives of the formula I2

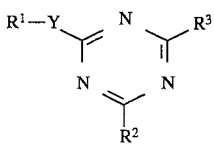

wherein
$R^1$ and Y have the meaning given and
$R^2$ and $R^3$ in each case independently of one another are alkoxy, alkylamino, arylamino or aryloxy having 1 to 10 C atoms;
c) Triazine derivatives of the formula Ia,

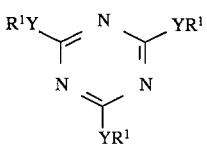

wherein Phe is an unsubstituted 1,4-phenylene group and X is H.
d) Triazine derivatives of the formulae I, I1, I2 and Ia, wherein Y is NH;
e) Triazine derivatives of the formula Ib

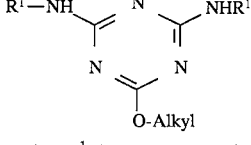

wherein $R^1$ has the meaning given and Alkyl is alkyl having 1 to 10 C atoms.
f) Triazine derivatives of the formula Ic

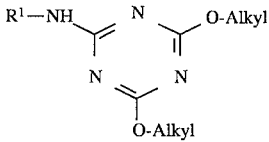

wherein $R^1$ has the meaning given and Alkyl is alkyl having 1 to 10 C atoms;
g) Triazine derivatives of the formula Id

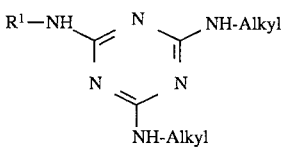

wherein $R^1$ has the meaning given and Alkyl is alkyl having 1 to 10 C atoms.
h) Triazine derivatives of the formula I,
wherein the radicals $R^2$ and $R^3$ are alkylamino or anilino,
Y is NH and Phe is a phenylene group which is substituted by 1 to 4, preferably 1 or 2, alkyl or alkoxy groups, or a 1,3-phenylene group;
i) Triazine derivatives of the formula I, wherein $R^2$ and $R^3$ are a radical of the formula Y-$R^1$;
j) Triazine derivatives of the formula I,
wherein $R^2$ is a radical of the formula Y-$R^1$ and $R^3$ is alkylamino, excluding the 2-ethylhexylamino group;
k) Triazine derivatives of the formula I
wherein X is $SO_3H$.

The phenylene group Phe is preferably a 1,4-phenylene group which is unsubstituted or substituted by one to four alkyl or alkoxy groups.

Preferably, the phenylene group is unsubstituted or substituted by one or two alkoxy groups having 1 to 8 C atoms, in particular by methoxy, ethoxy or 2-ethylhexyloxy groups.

Preferred compounds of the formula I are those of the formulae I3 to I18, wherein A is a group of the formula

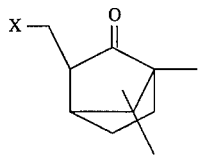

$R^4$ is alkyl or alkoxy having 1 to 10 C atoms and n is 1 or 2.

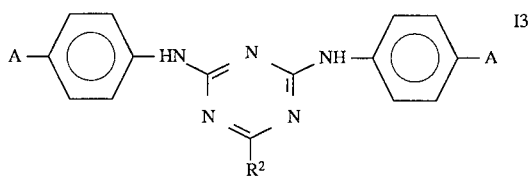

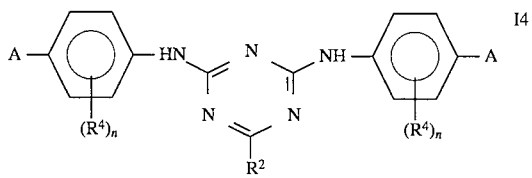

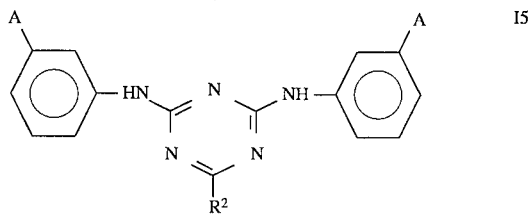

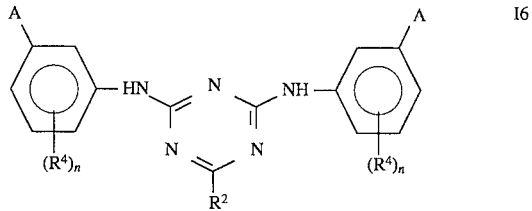

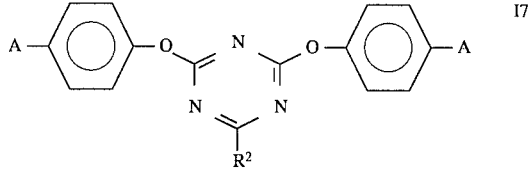

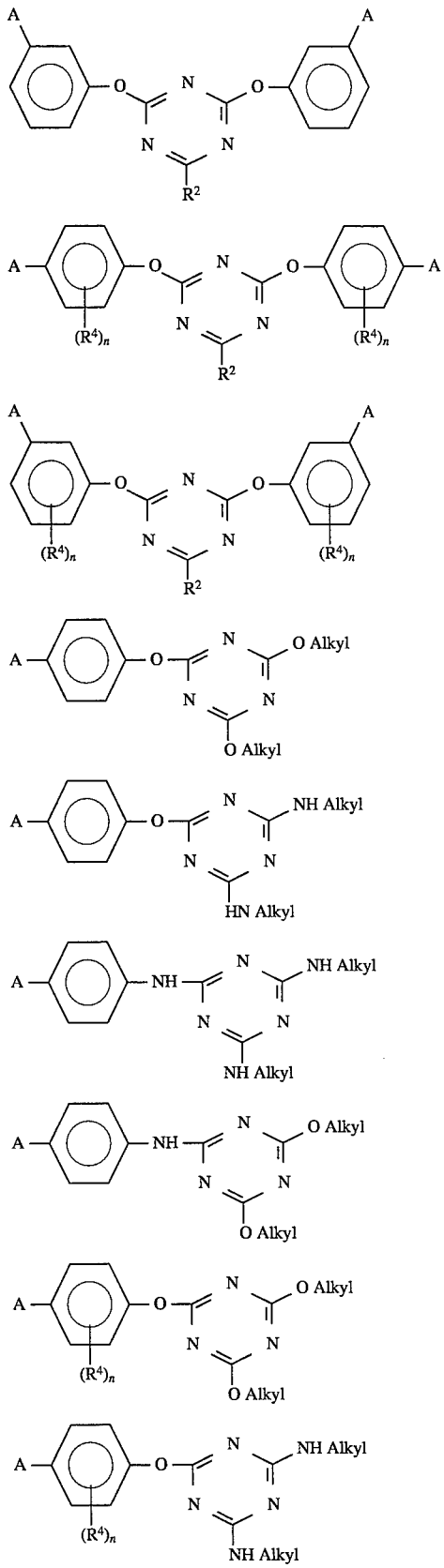
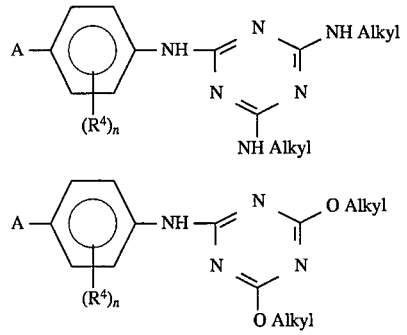
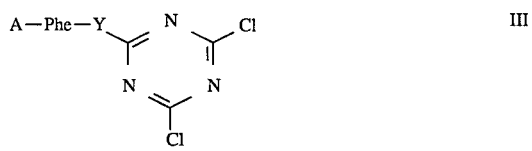
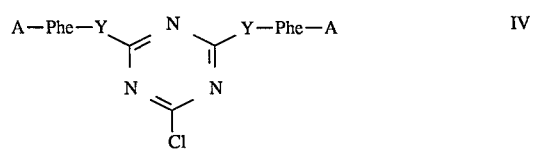

In the preferred compounds of the formula I3 to I18, $R^2$ preferably has the same meaning as the substituents in the 2- and 6-position or is an alkoxy, alkylamino, arylamino or aryloxy radical having 1 to 10 C atoms, in particular methoxy, ethoxy, 2-ethylhexyloxy, methylamino, ethylamino, 2-ethylhexylamino, anilino-, p-alkylanilino, O-alkylanilino, phenoxy, p-alkylphenoxy or o-alkylphenoxy.

The compounds of the formula I are obtained, for example, by a procedure in which an amino- or hydroxybenzylidenecamphor derivative of the formula II $$HY-Phe-A \qquad \qquad II$$

wherein Phe, A and Y have the meaning given, is reacted with cyanuric chloride.

If about 3 mol of the compound of the formula II are reacted with 1 mol of cyanuric chloride here at temperatures of between 20° C. and 150° C., preferably under reflux, in an inert solvent, the compound of the formula I wherein $R^2$ and $R^3$ are a radical of the formula $R^1$-Y is obtained.

If the reaction is carried out at low temperatures, that is to say between −40° C. and 80° C., preferably 0° C. and 60° C., in particular between 0° C. and room temperature, if appropriate in the presence of a weak base, with only about 1 mol of compound of the formula II per mole of cyanuric chloride, a triazine derivative of the formula III wherein A, Phe and Y have the meaning given, is intermediately obtained.

In the reaction of about 2 mol of compound of the formula II with cyanuric chloride at these temperatures, a triazine derivative of the formula IV wherein A, Phe and Y have the meaning given, is obtained as intermediate.

The compounds of the formula III and IV are new and the invention likewise relates to them.

The compound of the formula III or IV is then reacted with a further equivalent of a compound of the formula II wherein Y, Phe and/or A differ from the compound of the formula II originally employed, or with an alcohol, alkylamine, aniline or phenol having 1 to 10 C atoms.

The compounds of the formula I wherein $R^2$ differs from $R^1$-Y furthermore can be prepared by a procedure in which 1 mol of an alcohol, alkylamine, aniline or phenol of the formula $C_nH_{2n+1}$-(Phe)$_o$-Y-H, wherein o is 0 or 1 and n is 1 to 10, or if o=1, is 0–4, is reacted with 1 mol of cyanuric chloride in the presence of a base at temperatures of between −40° C. and +40° C., and the compound thus obtained, of the formula V

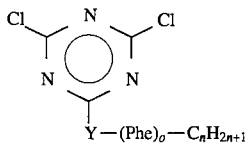

is then reacted with 2 equivalents of a compound of the formula II.

The compounds of the formula II are either known or can be prepared by methods known per se, for example by condensation of an amino- or hydroxybenzaldehyde with camphor or camphorsulfonic acid, for example by a method described in DE 40 27 980.

The invention also relates to the process for the preparation of the new compounds of the formula I.

The invention furthermore relates to a cosmetic formulation which comprises an active amount of at least one derivative of the above formula I in a cosmetically tolerated carrier.

Those cosmetic formulations wherein the carrier has at least one fatty phase and in the compound of the formula I X is H, or those wherein the carrier has at least one aqueous phase and X is $SO_3H$ are particularly preferred.

The cosmetic agents according to the invention can be used as agents for protection of the human epidermis or the hair or as sunscreen agents.

The invention furthermore relates to a method for protecting the skin and natural or sensitized hair from solar rays, an active amount of at least one compound of the formula I being applied to the skin or the hair.

"Sensitized hair" means hair which has been subjected to permanent wave treatment or a dyeing or decolorizing process.

The invention furthermore relates to a colored or noncolored light-stabilized cosmetic formulation which comprises an active amount of at least one benzylidenecamphor derivative of the above formula I.

If the cosmetic agent according to the invention is used as an agent for protection of the human epidermis from UV rays, it is in the various forms usually used for this type of agent. Thus, in particular, it can be in the form of oily or oily-alcoholic lotions, emulsions, for example as a cream or as a milk in the form of oily-alcoholic, oily-aqueous or aqueous-alcoholic gels, or as solid sticks, or can be made up as an aerosol.

It can comprise cosmetic adjuvants which are usually used in this type of agent, such as, for example, thickening agents, softening agents, moistening agents, surface-active agents, preservatives, agents against foam formation, perfumes, waxes, lanolin, propellants, dyestuffs and/or pigments, which color the agent itself or the skin, and other ingredients usually used in cosmetics.

The compound of the formula I is as a rule contained in an amount of 0.1 to 10% by weight, preferably 0.3 to 6% by weight, based on the total weight of the cosmetic agent for protection of the human epidermis.

An oil, wax or other fat substance, a lower monoalcohol or a lower polyol or mixtures thereof can be used as solubilizing agents. The particularly preferred monoalcohols or polyols include ethanol, i-propanol, propylene glycol, glycerol and sorbitol.

A preferred embodiment of the invention is an emulsion which is in the form of a protective cream or milk and, in addition to the compound of the formula I, comprises fatty alcohols, fatty acid esters, in particular triglycerides of fatty acids, fatty acids, lanolin, natural or synthetic oils or waxes and emulsifiers in the presence of water.

Further preferred embodiments are oily lotions based on natural or synthetic oils and waxes, lanolin and fatty acid esters, in particular triglycerides of fatty acids, or oily-alcoholic lotions based on a lower alcohol, such as ethanol, or a glycol, such as propylene glycol, and/or a polyol, such as glycerol, and oils, waxes and fatty acid esters, such as triglycerides of fatty acids.

The cosmetic agents according to the invention can also be in the form of an alcoholic gel which comprises one or more lower alcohols or polyols, such as ethanol, propylene glycol or glycerol, and a thickening agent, such as silica. The oily-alcoholic gels furthermore comprise natural or synthetic oil or wax.

The solid sticks comprise natural or synthetic waxes and oils, fatty alcohols, fatty acid esters, lanolin and other fatty substances.

The invention also relates to cosmetic sunscreen agents which comprise at least one compound of the formula I and can comprise other UVB and/or UVA filters.

In this case, the amount of filter of the formula I is as a rule between 0.2 and 8.0% by weight, preferably between 0.4 and 5.0% by weight, based on the total weight of the sunscreen agent.

If an agent is made up as an aerosol, the customary propellants, such as alkanes, fluoroalkanes and chlorofluoroalkanes, are as a rule used.

If the agent according to the invention is to protect natural or sensitized hair from UV rays, it can be in the form of a shampoo, lotion, gel or emulsion for rinsing out, the particular formulation being applied before or after shampooing, before or after coloring or decolorizing or before or after a permanent wave; or the agent is in the form of a lotion or gel for styling and treatment, as a lotion or gel for brushing or setting in a water wave, as a hair lacquer, permanent wave agent or coloring or decolorizing agent for the hair. In addition to the compound according to the invention, this agent can contain various adjuvants used in this type of agent, such as surface-active agents, thickening agents, polymers, softening agents, preservatives, foam stabilizers, electrolytes, organic solvents, silicone derivatives, oils, waxes, anti-fatting agents, dyestuffs and/or pigments, which color the agent itself or the hair, or other ingredients usually used for hair care. The agent as a rule contains 0.3 to 5.0% by weight of the compound of the formula I.

The present invention also relates to cosmetic agents which comprise at least one compound of the formula I as an agent for protection from UV rays and as an antioxidant; these agents include hair products, such as hair lacquers, water wave lotions for setting the hair, if appropriate for treatment or lighter styling, shampoos, color shampoos, hair coloring agents, cosmetic products, such as nail varnish, creams and oils for skin treatment, make-up (foundation), lipsticks, skin care agents, such as bath oils or creams, and other cosmetic agents which may present a problem in respect of their components in stability to light and/or oxidation in the course of storage. Such agents as a rule comprise 0.3 to 5.0% by weight of a compound of the formula I.

The invention furthermore relates to a process for protecting the cosmetic agents from UV rays and oxidation, an active amount of at least one compound of the formula I being added to these agents.

The invention furthermore relates to the use of the compounds of the formula I as solar filters having a wide absorption range in a wavelength range of from 280 to 400 nm, in particular those of the formula Ia in a range from 320 to 400 nm and those of the formula Ib in a range from 280 to 350 nm.

The invention furthermore relates to the use of the compounds of the formula I as cosmetic products.

As already mentioned above, the Applicant has found in the course of his studies that the compounds of the formula I display a significant pharmacological activity in the field of preventive treatment of inflammations and skin allergies.

The invention also relates to the compounds of the formula I for use as a medicament.

The invention furthermore relates to a pharmaceutical agent which comprises an active amount of at least one compound of the formula I as an active compound in a non-toxic carrier or excipient.

The pharmaceutical agents according to the invention can be administered orally or topically.

For oral administration, the pharmaceutical agent is in the form of lozenges, gelatin capsules or coated tablets, or as a syrup, suspension, solution, emulsion and the like. For topical administration, it is in the form of an ointment, cream, pomade, solution, lotion, gel, spray, suspension and the like.

This agent can comprise inert or pharmacodynamically active additives, in particular hydrating agents, antibiotics, steroidal or nonsteroidal anti-inflammatory agents, carotenoids and agents against psoriasis.

This agent can also comprise flavor-improving agents, preservatives, stabilizers, moisture regulators, pH regulators, modifiers for the osmotic pressure, emulsifiers, local anaesthetics, buffers and the like.

It can furthermore be formulated in a manner known per se in a sustained release form or in a form in which the active compound is released rapidly.

Even without further statements, it is assumed that an expert can utilize the above description in the broadest sense. The preferred embodiments are therefore to be interpreted only as a descriptive and in no way in any manner limiting disclosure.

The complete disclosure of all the Applications, patents and publications mentioned above and below and of the corresponding Applications P 42 04 923, filed on 19 Feb. 1992, and P 42 23 890, filed on 21 Jul. 1992, is incorporated in this Application by reference.

The following examples are representative for the present invention.

The extinction is determined at the wavelength stated at a cell thickness of 1 cm.

EXAMPLE 1

2,4,6-Tris(4-camphylidenemethylene-anilino)- 1,3,5-triazine 6 g (33 mmol) of cyanuric chloride in 200 ml of toluene are added dropwise to a solution of 25.5 g (0.1 mol) of 4-amino-benzylidenecamphor in 500 ml of toluene at 0° C. The reaction mixture is heated under reflux. When the reaction has ended, the white solid which has precipitated out is filtered off with suction, rinsed and stirred thoroughly.

Melting point: 336° C. The further spectra correspond to the expected compound.

UV (ethanol, c=1 mg/100 ml): $\lambda_{max}$=354 nm, E=1.2

The following are prepared analogously:
2,4,6-Tris[3-camphylidenemethylene-anilino]-1,3,5-triazine
2,4,6-Tris[4-(camphylidenemethylene)-2-methoxyanilino]-1,3,5-triazine
2,4,6-Tris[3-(camphylidenemethylene)-2-methoxyanilino]-1,3,5-triazine
2,4,6-Tris[4-(camphylidenemethylene)-3-methoxyanilino]-1,3,5-triazine
2,4,6-Tris[4-(camphylidenemethylene)-3-(2-ethylhexyloxy)anilino]-1,3,5-triazine

EXAMPLE 2

2,4,6-Tris(camphylidene-methylenephenyl-4-oxy)- 1,3,5-triazine 7.7 g (30 mmol of 2-(4-hydroxy-benzylidene)camphor in 100 ml of a 1 molar NaOH solution are added dropwise to a solution of 1.8 g (10 mmol) of cyanuric chloride in 100 ml of methylene chloride and the mixture is heated under reflux. When the reaction has ended, the organic phase is separated off and rinsed with water. The white crystals formed show the expected spectra.

UV (ethanol, c=1 mg/100 ml): $\lambda_{max}$=295 nm, E=0.98

The following are prepared analogously:
2,4,6-Tris[4-(camphylidenemethylene)-3-methoxyphenoxy]- 1,3,5-triazine
2,4,6-Tris[3-(camphylidenemethylene)-phenoxy]- 1,3,5-triazine
2,4,6-Tris[4-(camphylidenemethylene)-2-methoxyphenoxy]- 1,3,5-triazine

EXAMPLE 3

2,4-Bis(2-ethyl-hexylamino)-6-(4-camphylidenemethylene-anilino)- 1,3,5-triazine a) 2-(4-Camphylidenemethylene-anilino)-4,6-dichloro- 1,3,5-triazine 0.1 mol of 4-aminobenzylidenecamphor, dissolved in toluene, is added dropwise to a solution of 0.1 mol of cyanuric chloride in toluene. The reaction mixture is heated to 40° C. Working-up leads to 36 g (88%) of a pale yellow solid. Melting point: 238° C.

b) 2,4-Bis(2-ethyl-hexylamino)-6-(4-camphylidenemethylene-anilino)- 1,3,5-triazine A reaction mixture comprising 33 g (0.26 mol) of 2-ethylhexylamine and 50 g (0.12 mol) of 2-(4-camphylidenemethylene-anilino)- 4,6-dichloro-1,3,5-triazine in toluene is heated to 90° C. in the presence of sodium acetate. When the starting materials have reacted completely, the mixture is worked up. The product (95%) is a yellow viscous oil. UV (ethanol, c=1 mg/100 ml): $\lambda_{max}$=345 nm, E=0.57.

EXAMPLE 4

2,4-Bis-ethoxy-6-(4-camphylidenemethylene-anilino)- 1,3,5-triazine 0.05 mol of 2-(4-camphylidenemethylene-anilino)- 4,6-dichloro-1,3,5-triazine (see Example 3a) is added to a solution of 0.3 mol of sodium ethanolate in ethanol and the mixture is heated to 60° C. After working up, the product is obtained as white crystals (melting point: 161° C.) in a yield of 63%.

UV (ethanol, c=1 mg/100 ml): $\lambda_{max}$=335 nm, E=0.90.

EXAMPLE 5

2,4-Bis(2-ethyl-hexyloxy)-6-(4-camphylidenemethylene-anilino)- 1,3,5-triazine a) 2,4-Bis(2-ethyl-hexyloxy)-6-chloro-1,3,5-triazine By dropwise addition of 47 ml (0.3 mol) of 2-ethyl-hexanol to a suspension of 0.3 mol of potassium hydride in tetrahydrofuran and subsequent heating, the potassium salt of the alcohol is prepared. The solution is slowly added dropwise to a solution of cyanuric chloride (0.13 mol) in tetrahydrofuran at 0° C. After the mixture has been subsequently stirred at 20° C. for two hours, it is worked up. Distillation leads to 23 g (41%) of pure product. Boiling point=181° C./0.022 mm Hg.

b) 2,4-Bis(2-ethyl-hexyloxy)-6-(4-camphylidenemethylene-anilino)- 1,3,5-triazine 0.1 mol of 4-aminobenzylidenecamphor is added to a solution of 0.1 mol of 2,4-bis(2-ethyl-hexyloxy)- 6-chloro-1,3,5-triazine in toluene and the mixture is heated at 90° C. until the reaction is complete. Working-up leads to 55 g (94%) of a yellow viscous oil.

UV (ethanol, c=1 mg/100 ml): $\lambda_{max}$=334 nm, E=0.64

The following are [sic] prepared analogously: 2,4-Bis(phenoxy)-6-(4-camphylidenemethylene-anilino)- 1,3,5-triazine, UV (ethanol, c=1 mg/100 ml): $\lambda_{max}$=335 nm, E=0.71, melting point: 207° C.

EXAMPLE 6

2,4-Bis(4-camphylidenemethylene-anilino)- 6-ethoxy-1,3,5-triazine a) 2,4-Bis(4-camphylidenemethylene-anilino)- 6-chloro-1,3,5-triazine To a solution of cyanuric chloride in toluene is slowly added dropwise 4-aminobenzylidene-camphor (molar ratio 1:2), likewise in toluene, and the mixture is heated to 60° C. while monitoring by thin layer chromatography. After working up, the abovementioned compound is obtained to the extent of 45%. Melting point: 221° C.

b) 2,4-Bis(4-camphylidenemethylene-anilino)- 6-ethoxy-1,3,5-triazine 2,4-Bis(4-camphylidenemethylene-anilino)- 6-chloro-1,3,5-triazine is reacted with sodium ethanolate analogously to the instructions of Example 2. The desired product forms to the extent of 43%.

UV (ethanol, c=1 mg/100 ml): $\lambda_{max}$=346 nm, E=0.95, melting point: 198° C.

EXAMPLE 7

2,4-Bis(4-camphylidenemethylene-anilino)- 6-propyloxy-1,3-5-triazine

A solution of 0.2 mol of 4-aminobenzylidenecamphor in toluene is added to a mixture of 0.1 mol of 2,4-dichloro-6-propyloxy-1,3,5-triazine in toluene and the mixture is heated to 94° C. Working-up leads to 31 g (48%) of white crystals. Melting point: 164° C.

UV (ethanol, c=1 mg/100 ml): $\lambda_{max}$=345 nm, E=0.94

The following compounds were synthesized analogously to examples 6 and 7:

2,4-Bis(4-camphylidenemethylene-anilino)-6-butyloxy-1,3,5-triazine
UV (ethanol, c=1 mg/100 ml): $\lambda_{max}$=345 nm, E=0.88, melting point: 181° C.

2,4-Bis(4-camphylidenemethylene-anilino)-6-phenoxy-1,3,5-triazine
UV (ethanol, c=1 mg/100 ml): $\lambda_{max}$=348 nm, E=0.95, melting point: 185° C.

2,4-Bis(4-camphylidenemethylene-anilino)-6-(2-ethlyhexyloxy)-1,3,5-triazine was obtained analogously to example 5. In the first reaction stage, the two components were chosen in a molar ratio of 1:1.

UV (ethanol, c=1 mg/100 ml): $\lambda_{max}$=345 nm; E=0.84, melting point: 127° C.

EXAMPLE 8

| Sunscreen cream (water-in-oil) | | % |
|---|---|---|
| A 2,4,6-Tris(4-camphylidene-methylene-anilino)-1,3,5-triazine | (1) | 0.50 |
| Arlacel 581 | (2) | 6.00 |
| Viscous paraffin (Art. no. 7160) | (1) | 17.50 |
| Beeswax, bleached (Art. no. 11544) | (1) | 3.00 |
| Miglyol 812 | (3) | 11.50 |
| Dow Corning 200 (100 cs) | (4) | 2.00 |
| Tocopherolacetate (Art. no. 500952) | (1) | 0.50 |
| B Glycerol (Art. no. 4093) | (1) | 2.00 |
| Magnesium sulfate heptahydrate (Art. no. 5882) | (1) | 0.70 |
| Preservative | | q.s |
| Water, demineralized | | to 100.00 |

Preparation:

Heat phase A to 75° C. and phase B to 80° C. Stir phase B slowly into phase A. Homogenize. Cool, while stirring. If appropriate, perfume at 40° C.

Sources of supply:
(1) E. Merck, Darmstadt
(2) ICI, Essen
(3) Hüls Troisdorf AG, Witten
(4) Dow Corning, Düsseldorf

EXAMPLE 9

| Sunscreen cream (water-in-oil) | | % |
|---|---|---|
| A 2,4,6-Tris(4-camphylidene-methylenephenoxy)-1,3,5-triazine | (1) | 0.50 |
| Arlacel 581 | (2) | 6.00 |
| Viscous paraffin (Art. no. 7160) | (1) | 17.50 |
| Beeswax, bleached (Art. no. 11544) | (1) | 3.00 |
| Miglyol 812 | (3) | 11.50 |
| Dow Corning 200 (100 cs) | (4) | 2.00 |
| Tocopherolacetate (Art. no. 500952) | (1) | 0.50 |
| B Glycerol (Art. no. 4093) | (1) | 2.00 |
| Magnesium sulfate heptahydrate (Art. no. 5882) | (1) | 0.70 |
| Preservative | | q.s |
| Water, demineralized | | to 100.00 |

Preparation:

Heat phase A to 75° C. and phase B to 80° C. Stir phase B slowly into phase A. Homogenize. Cool, while stirring. If appropriate, perfume at 40° C.

Sources of supply:
(1) E. Merck, Darmstadt
(2) ICI, Essen
(3) Hüls Troisdorf AG, Witten
(4) Dow Corning, Düsseldorf

EXAMPLE 10

| Sunscrean milk (water-in-oil) | | % |
|---|---|---|
| A 2,4,6-Tris(4-camphylidene-methylene-anilino)-1,3,5-triazine | (1) | 0.50 |
| Abil WE 09 | (2) | 5.00 |
| Highly liquid paraffin (Art. no. 7174) | (1) | 16.00 |
| B Sodium chloride (Art. no. 6400) | (1) | 2.00 |
| Glycerol (Art. no. 4093) | (1) | 3.00 |
| Preservative | | q.s |
| Water, demineralized | | to 100.00 |
| C Delaila perfume oil | (3) | 0.50 |

Preparation:
Heat phase A to 75° C. and phase B to 80° C. Phase B is stirred slowly into phase A. Homogenize. Cool, while stirring, and add phase C at 40° C.
Sources of supply:
(1) E. Merck, Darmstadt
(2) Th. Goldschmidt, Essen
(3) Dragoco, Hozminden

EXAMPLE 11

| Sunscreen milk (water-in-oil) | | % |
|---|---|---|
| A 2,4,6-Tris(4-camphylidene-methylene-phenoxy)-1,3,5-triazine | (1) | 0.50 |
| Abil WE 09 | (2) | 5.00 |
| Highly liquid paraffin (Art. no. 7174) | (1) | 16.00 |
| B Sodium chloride (Art. no. 6400) | (1) | 2.00 |
| Glycerol (Art. no. 4093) | (1) | 3.00 |
| Preservative | | q.s |
| Water, demineralized | | to 100.00 |
| C Delaila perfume oil | (3) | 0.50 |

Preparation:
Heat phase A to 75° C. and phase B to 80° C. Phase B is stirred slowly into phase A. Homogenize. Cool, while stirring, and add phase C at 40° C.
Sources of supply:
(1) E. Merck, Darmstadt
(2) Th. Goldschmidt, Essen
(3) Dragoco, Holzminden

EXAMPLE 12

| Sunscreen cream (oil-in-water) | | % |
|---|---|---|
| A 2,4,6-Tris(4-camphylidene-methylene-anilino)-1,3,5-triazine | (1) | 0.50 |
| Brij 72 | (2) | 1.00 |
| Arlacel 165 | (2) | 5.00 |
| Liquid paraffin (Art. no. 7162) | (1) | 15.00 |
| Cetyl alcohol (Art. no. 989) | (1) | 2.50 |
| Miglyol 812 | (3) | 4.00 |
| Isopropyl myristate | (4) | 2.00 |
| B Glycerol (Art. no. 4093) | (1) | 4.00 |
| Karion F liquid (Art. no. 2993) | (1) | 5.00 |
| Preservative | | q.s |
| Water, demineralized | | to 100.00 |
| C Wimbledon perfume oil | (5) | 0.40 |

Preparation:
Heat phase A to 75° C. and phase B to 80° C. Phase B is stirred slowly into phase A. Homogenize. Cool, while stirring, and add phase C at 40° C.
Sources of supply:
(1) E. Merck, Darmstadt
(2) ICI, Essen
(3) Hüls Troisdorf AG, Witten
(4) Henkel, Düsseldorf
(5) Haarmann & Reimer, Holzminden

EXAMPLE 13

| Sunscreen cream (oil-in-water) | | % |
|---|---|---|
| A 2,4,6-Tris(4-camphylidene-methylene-phenoxy)-1,3,5-triazine | (1) | 0.50 |
| Brij 72 | (2) | 1.00 |
| Arlacel 165 | (2) | 5.00 |
| Liquid paraffin (Art. no. 7162) | (1) | 15.00 |
| Cetyl alcohol (Art. no. 989) | (1) | 2.50 |
| Miglyol 812 | (3) | 4.00 |
| Isopropyl myristate | (4) | 2.00 |
| B Glycerol (Art. no. 4093) | (1) | 4.00 |
| Karion F liquid (Art. no. 2993) | (1) | 5.00 |
| Preservative | | q.s |
| Water, demineralized | | to 100.00 |
| C Wimbledon perfume oil | (5) | 0.40 |

Preparation:
Heat phase A to 75° C. and phase B to 80° C. Stir phase B slowly into phase A. Homogenize. Cool, while stirring, and add phase C at 40° C.
Sources of supply:
(1) E. Merck, Damstadt
(2) ICI, Essen
(3) Hüls Troisdorf AG, Witten
(4) Henkel, Düsseldorf
(5) Harrmann & Reimer, Holzminden

We claim:
1. A triazine compound of the formula I

$$\begin{array}{c} R^1-Y \\ \phantom{xxx} \diagdown \\ \phantom{xxxx} N \phantom{xx} R^3 \\ \phantom{xxx} \diagup \phantom{x} \diagdown \\ \phantom{xx} N \phantom{xxxx} N \\ \phantom{xxxxx} \diagdown \phantom{x} \diagup \\ \phantom{xxxxxx} R^2 \end{array} \quad I$$

wherein
Y is NH or O,
$R^1$ in each case independently of one another are a radical of the formula II $$-Phe-CH= \text{(camphor ketone with X substituent)} \quad II$$

wherein

Phe is a phenylene group which is unsubstituted or substituted by 1 to 4 alkyl or alkoxy groups having 1 to 10 C atoms and
X is H or —SO$_3$H,
and
R$^2$ and R$^3$
 in each case independently of one another are a radical of the formula Y-R$^1$,
or
 alkoxy, alkylamino, arylamino or aryloxy having 6 to 10 C atoms, provided that when one of the R$_2$ or R$_3$ is Y-R$^1$ the other is aryloxy having 6 to 10 C atoms.

2. A triazine compound of the formula I1 according to claim 1

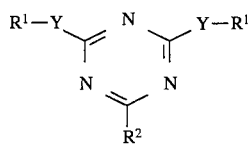

wherein R$^1$, R$^2$ and Y have the meaning given.

3. A triazine compound of the formula I2 according to claim 1

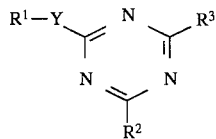

wherein
R$^1$ and Y have the meaning given and
R$^2$ and R$^3$ in each case independently of one another are alkoxy, alkylamino, arylamino or aryloxy having 6 to 10 C atoms.

4. A triazine compound according to claim 1, of the formula Ia

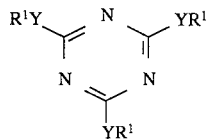

wherein Phe is an unsubstituted 1,4-phenylene group and X is H.

5. A triazine compound according to claim 1, wherein Y is NH.

6. A triazine compound according to claim 3 of the formula Ic

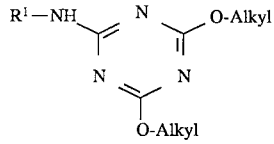

wherein R$^1$ has the meaning given and
Alkyl is alkyl having 1 to 10 C atoms.

7. A triazine compound according to claim 3 of the formula Id

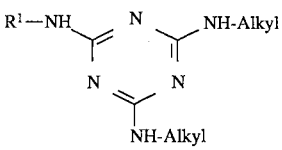

wherein R$^1$ has the meaning given and Alkyl is alkyl having 1 to 10 C atoms.

8. A triazine compound of formula I of claim 1 wherein R$^2$ and R$^3$ are alkylamino or anilino, and Y is NH.

9. A triazine compound of formula I of claim 1, wherein X is SO$_3$H.

10. A medicament composition comprising a compound of the formula I of claim 1.

11. A cosmetic formulation, which in that it comprises an active amount of at least one compound of the formula I according to claim 1 in a cosmetically tolerated carrier.

12. A cosmetic formulation according to claim 11, wherein the carrier contains at least one fatty phase, and which comprises at least one compound of the formulae Ia, Ic or Id.

13. A cosmetic formulation according to claim 11, which comprises 0.1 to 10% by weight of at least one compound of the formula I.

14. A cosmetic formulation according to claim 11, which comprises 0.4 to 1.0% by weight of at least one compound of the formula I.

15. A cosmetic formulation according to claim 11, which comprises about 0.5% by weight of at least one compound of the formula I.

16. A method for protecting the skin or hair from exposure to the sun which comprises applying thereto a composition comprising a compound of the formula I of claim 1, in an amount effective to protect the skin or hair from exposure to the sun.

17. A method for preventive treatment of inflammations and allergies of the skin comprising applying thereto a composition comprising a compound of the formula I of claim 1, in an amount effective to prevent inflammations and allergies of the skin.

18. A method for preventive treatment of cancers caused by exposure to the sun which comprises applying to the skin a composition comprising a compound of the formula I of claim 1, in an amount effective to prevent cancers caused by exposure to the sun.

19. A pharmaceutical formulation comprising an active amount of at least one compound of the formula I of claim 1 and a physiologically acceptable carrier or excipient.

20. A pharmaceutical formulation according to claim 19, which is in a form for topical application.

* * * * *